(12) United States Patent
Richter et al.

(10) Patent No.: US 12,108,966 B2
(45) Date of Patent: Oct. 8, 2024

(54) MULTIOPTIONAL ACCESS DEVICE

(71) Applicant: DePuy Synthes Products, Inc., Raynham, MA (US)

(72) Inventors: Jörn Richter, Oberdorf Basel-Landschaft (CH); Daniela Wehrli, Oberdorf Basel-Landschaft (CH); Christopher Cromer, Boston, MA (US); Samuel Jacobs, Acton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 119 days.

(21) Appl. No.: 17/542,133

(22) Filed: Dec. 3, 2021

(65) Prior Publication Data

US 2023/0172631 A1 Jun. 8, 2023

(51) Int. Cl.
*A61B 17/34* (2006.01)
*A61B 17/17* (2006.01)
(Continued)

(52) U.S. Cl.
CPC .......... *A61B 17/3423* (2013.01); *A61B 17/17* (2013.01); *A61B 17/3496* (2013.01);
(Continued)

(58) Field of Classification Search
CPC ..... A61B 17/3423; A61B 17/30; A61B 17/17; A61B 17/3496
See application file for complete search history.

(56) References Cited

U.S. PATENT DOCUMENTS

2009/0149857 A1\* 6/2009 Culbert ................ A61B 1/0684
606/191
2017/0333057 A1 11/2017 Kostrzewski et al.
(Continued)

FOREIGN PATENT DOCUMENTS

| CN | 111956330 A | 11/2020 |
|---|---|---|
| EP | 3662858 A1 | 6/2020 |
| EP | 3799805 A2 | 4/2021 |

*Primary Examiner* — Sameh R Boles
(74) *Attorney, Agent, or Firm* — Condo Roccia Koptiw LLP (57) ABSTRACT

Systems, methods, and devices are disclosed for robotic surgical systems including a robotic arm, the systems comprising an end effector attached to the robotic arm and retaining an access guide, and an initial access tool detachably connected to the access guide, wherein the initial access tool comprises a housing, a shaft extending from the housing coaxially through the access guide, and a distal tip attached to the shaft and protruding from a portion of the access guide distal to the end effector, wherein the housing is adapted to prevent rotation with respect to the access guide. In some embodiments, the access guide is adapted to retain an initial access tool and one or more of a burring tool, a drilling tool, or a tapping tool. In some embodiments, the initial access tool further comprises a step spaced from a distal end of the shaft, a rigid sleeve for placing over the shaft below the step, a spring for placing over the shaft below the step, and at least one detachable tip for engaging the distal end of the shaft, wherein the housing is adapted to prevent rotation with respect to the access guide.

20 Claims, 7 Drawing Sheets

(51) Int. Cl.
*A61B 34/30* (2016.01)
*A61B 34/20* (2016.01)

(52) U.S. Cl.
CPC ...... *A61B 34/30* (2016.02); *A61B 2017/3456* (2013.01); *A61B 2034/2072* (2016.02)

(56) References Cited

U.S. PATENT DOCUMENTS

| | | | |
|---|---|---|---|
| 2020/0170723 A1* | 6/2020 | Crawford | A61N 1/0539 |
| 2020/0315737 A1 | 10/2020 | Crawford et al. | |
| 2021/0113348 A1 | 4/2021 | Lopez | |
| 2022/0330950 A1* | 10/2022 | Glerum | A61B 17/3423 |
| 2023/0013550 A1* | 1/2023 | Brik | A61B 34/25 |

\* cited by examiner

MULTIOPTIONAL ACCESS DEVICE

BACKGROUND

A computer-assisted surgical system may include a robot arm, controller, and navigational system. Robotic or robot-assisted surgeries have many associated advantages, particularly in terms of precise placement surgical tools and/or implants. For example, in surgeries where multiple steps are carried out, such as, by way of a non-limiting example, a drill, tap, and screw technique, the conceptual ability of a robotic surgical system to track a position and/or orientation of a first tool to achieve a desired trajectory and then later precisely return to the same position and/or orientation with a second tool at a desired trajectory is particularly advantageous.

However, changes introduced into the computer-assisted surgical system, such as by changing end effectors for the robot arm, may increase the chance of misalignment or introduce other sources of error. By way of a nonlimiting example, errors can result in a variety of disadvantages, including loss of sterility by damaging the drape. Accordingly, there is a need for systems, devices, and methods that improve computer-assisted surgical systems, for example, by developing end effectors that are adapted to removably retain a number of different tools (e.g., a series of tools for use in a procedure) without affecting navigational precision.

SUMMARY

Systems, methods, and devices are described for robotic surgical systems including a robotic arm, the systems comprising an end effector attached to the robotic arm and retaining an access guide, and an initial access tool detachably connected to the access guide, wherein the initial access tool comprises a housing, a shaft extending from the housing coaxially through the access guide, and a distal tip attached to the shaft and protruding from a portion of the access guide distal to the end effector, wherein the housing is adapted to prevent rotation with respect to the access guide. In some embodiments, the access guide is adapted to retain an initial access tool and one or more of a burring tool, a drilling tool, or a tapping tool.

Also described are methods, comprising providing a robotic surgical system comprising a robotic arm, an end effector attached to the robotic arm and retaining an access guide, wherein the access guide is adapted to retain an initial access tool and one or more of a burring tool, a drilling tool, or a tapping tool, a navigational array attached to the end effector, and a controller configured to operate the robotic arm to position end effector, accessing a bone surface of a patient, contacting the bone surface with the initial access tool, and contacting the bone surface with the one or more of the burring tool, the drilling tool, or the tapping tool.

Also described are instrument sets for use with a robotic surgical system, the set comprising an access guide, an initial access tool comprising a housing and a shaft extending from the housing and having a step spaced from a distal end of the shaft, a rigid sleeve for placing over the shaft below the step, a spring for placing over the shaft below the step, and at least one detachable tip for engaging the distal end of the shaft, wherein the housing is adapted to prevent rotation with respect to the access guide.

DETAILED DESCRIPTION

Figure 1:
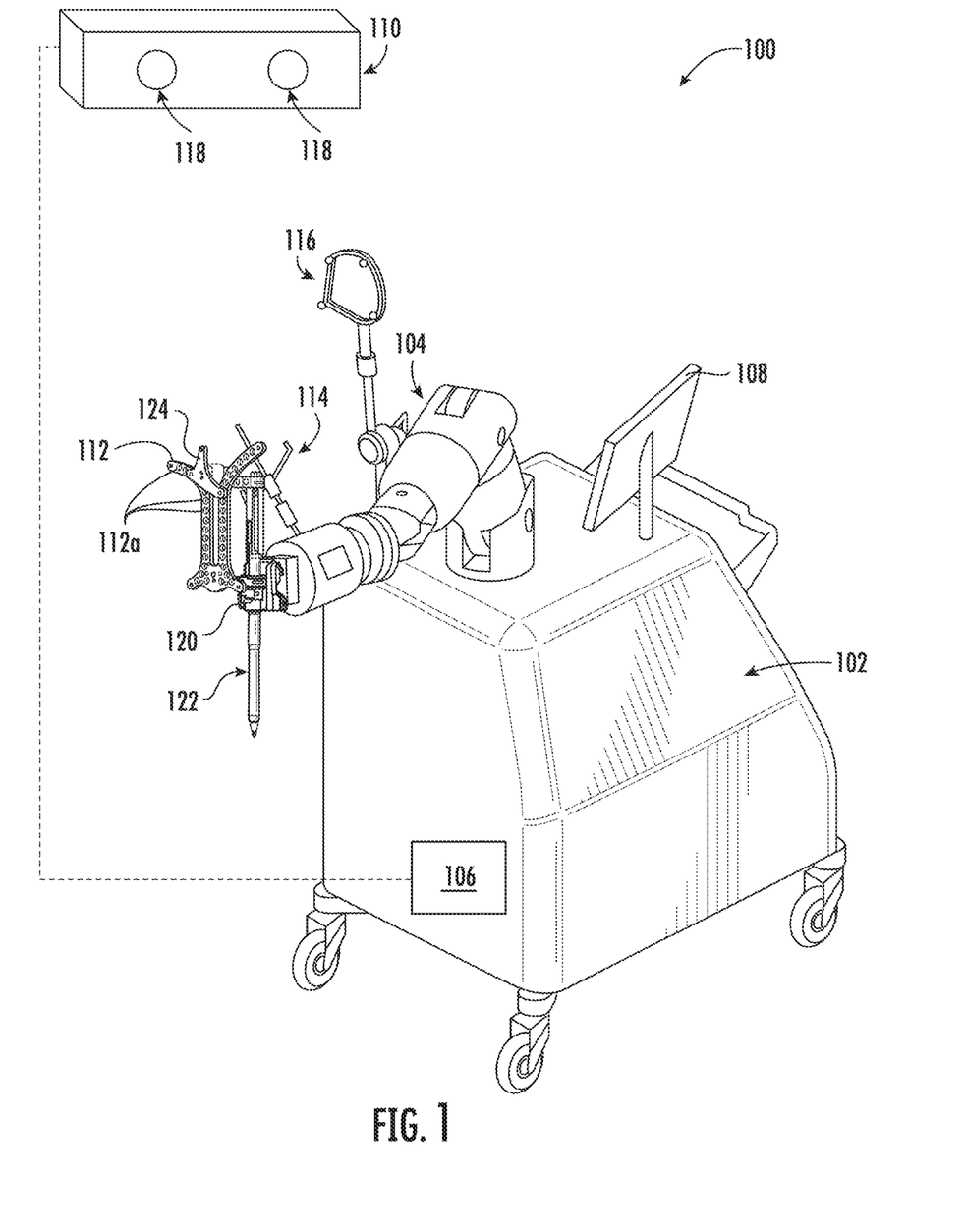
FIG. 1 shows a schematic of a computer-assisted surgical system including a surgical robot arm and an end effector.

FIG. 1 shows an overview of a computer-assisted surgical system 100. A surgical robot base 102 supports a robot arm 104. The base 102 is depicted as a mobile base, but stationary bases are also contemplated. The robot arm 104 includes a plurality of arm segments connected by rotatable or otherwise articulating joints and may be moved by actuation of the joints, locked in place, etc. The robot arm 104 to move in all six degrees of freedom during a surgical procedure. The robot arm 104 may be configured for incremental changes (e.g., in each of the six degrees of freedom) to ensure the necessary precision during surgery. The robot arm 104 may actively move about the joints to position arm in a desired position relative to the patient (not depicted), or the robot arm may be set and locked into a position. For example, the present disclosure is contemplated to include use of tools by surgical robots, by users with some degree of robotic assistance, and without involvement of surgical robots or robotic assistance (e.g., once positioned and locked).

A control unit or controller 106 controls the robot arm 104 and associated navigational system(s). The controller 106 typically includes a power supply, AC/DC converters, motion controllers to power the motors of the actuation units in each joint, fuses, real-time interface circuits, and other components conventionally included in robotic surgical systems. An external device 108 may communicate with the controller 106. The device 108 may be a display, a computing device, remote server, etc., configured to allow a surgeon or other user to input data directly into the controller 106. Such data may include patient information and/or surgical procedure information. The device 108 may display information from the controller, such as alerts. Communication between the device 108 and the controller 106 may be wireless or wired.

The system 100 may also comprise a navigational system that includes a tracking unit 110, such that the relative pose or three-dimensional position and orientation of fiducials attached to a plurality of the navigational system navigation arrays (e.g., a navigation array 112, a navigation array 114, and an optional navigation array 116 (and/or other navigation arrays)) may be tracked in real time and shared to the controller 106 for planning or control. The tracking unit 110 may measure the relative motions between any and all components coupled to navigation arrays in a known manner. Tracking may be performed in a number of ways, e.g., using stereoscopic optical detectors 118, ultrasonic detectors, sensors configured to receive position information from inertial measurement units, etc. Tracking in real time, in some embodiments, means high frequencies greater than twenty Hertz, in some embodiments in the range of one hundred to five hundred Hertz, with low latency, in some embodiments less than five milliseconds. Regardless of how it is gathered, position and orientation data may be transferred between components (e.g., to the controller 106) via any suitable connection, e.g., with wires or wirelessly using a low latency transfer protocol. The real-time controller 106 may carry out real-time control algorithms at a reasonably high frequency with low additional latency to coordinate movement of the system 100. The tracking unit may also include cameras, or use the stereoscopic optical detectors 116, to detect, for example, characteristics of end effectors attached to the robot arm 104.

Fiducials (not depicted) of the navigational system may be attached to the navigation arrays (e.g., the navigation array 112, the navigation array 114, and/or optional navigation array 116 (and/or other navigation arrays)), for example, via a plurality of mounting points 112a (e.g., of the navigation array 112). Fiducials may be arranged in predetermined positions and orientations with respect to one another. The fiducials may be aligned to lie in planes of known orientation (e.g., perpendicular planes, etc.) to enable setting of a Cartesian reference frame. The fiducials may be positioned within a field of view of a navigation system and may be identified in images captured by the navigation system. The fiducials may be single-use reflective navigation markers. Exemplary fiducials include infrared reflectors, light emitting diodes (LEDs), spherical reflective markers, blinking LEDs, augmented reality markers, and so forth. The navigation arrays may be or may include an inertial measurement unit (IMU), an accelerometer, a gyroscope, a magnetometer, other sensors, or combinations thereof. The sensors may transmit position and/or orientation information to a navigation system, e.g., to a processing unit of the navigation system, which may be, for example, the controller 106.

The navigation array 114 may be mounted on the robot arm 104 to determine a position of the robot arm or a distal portion thereof (indicative of an end effector position or with reference to a difference from a position of the navigation array 112). The structure and operation of the navigation array 114 may vary depending on the type of navigation system used. In some embodiments, the navigation array 114 may include one or more sphere-shaped or other fiducials for use with an optical navigation system, for example, a robotic navigation system. The navigation system may facilitate registering and tracking of the position and/or orientation of the navigation array 114 and, by extension, an end effector 120 and its relative distance to other objects in the operating room, e.g., a patient, a surgeon, etc.

Figure 3:
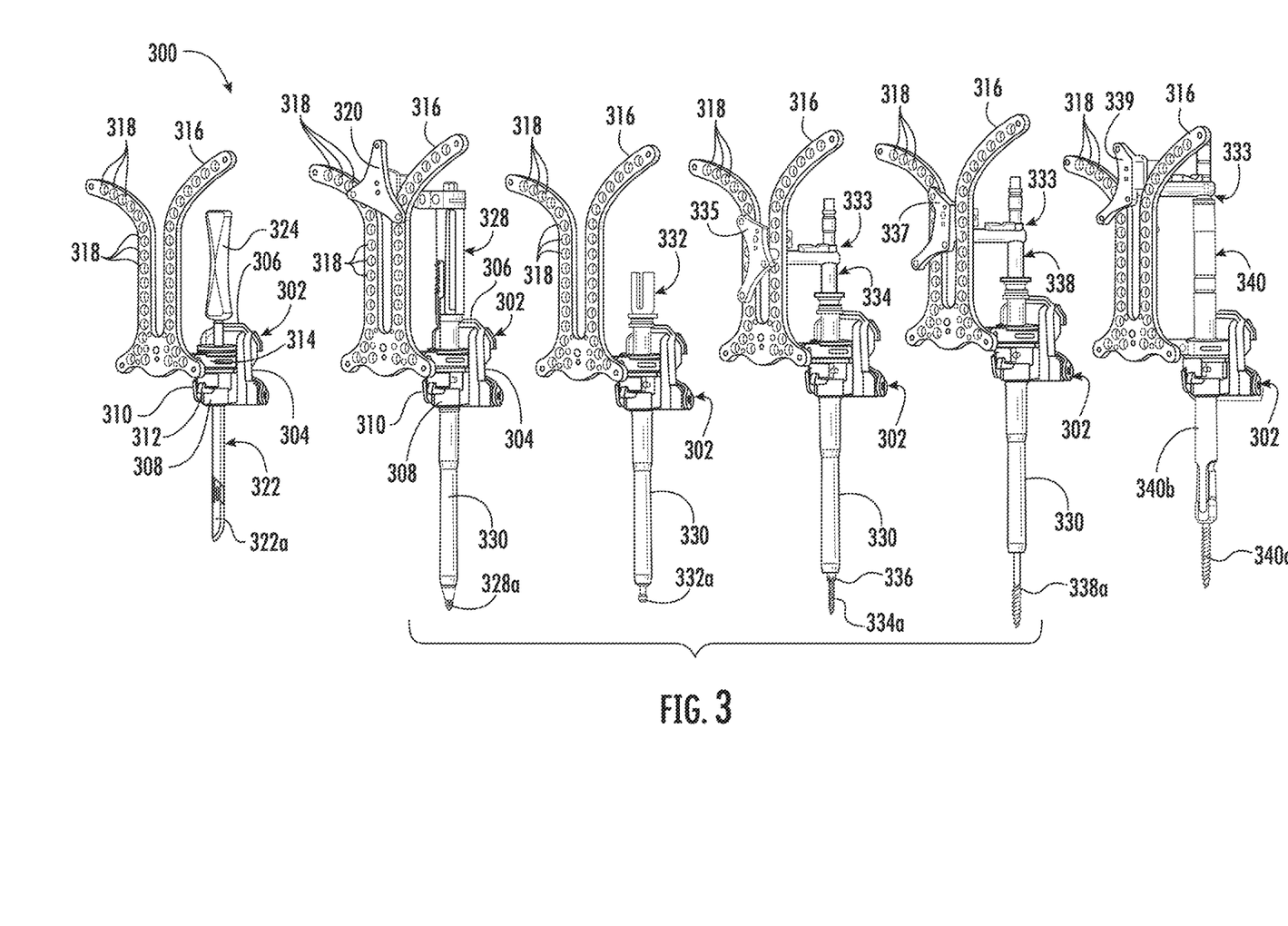
FIG. 3 shows a plurality of tools retained by an end effector which may be used (e.g., sequentially) in an exemplary surgical workflow.

The end effector 120 may be coupled to the robot arm 104, for example, via an end plate locked by a lever. As can be appreciated, there should be no play between the end effector 102 and robot arm 104. While the system 100 may utilize end effectors of various shapes, sizes, and functionalities, the depicted end effector has an aperture for removably retaining a tool 122. In some embodiments, the end effector 120 is part of a Universal Navigation Adaptor Set (UNAS) and the navigation array 112 is mounted to the end effector. Advantageously, the end effector 120 may be adapted to retain a series of tools including the tool 122 (for example, a series of tools used in a particular surgical procedure, such as depicted in FIG. 3).

The tool 122 may be placed in a guide (e.g., or other aperture) of the end effector 120. A locking mechanism of the end effector 120 may secure the tool 122 in place. The locking mechanism may be a slider locking mechanism or other feature. The tool 122 as depicted is a dilator, but it is understood that the tool may have at a distal end: a probe, a dilator tip (e.g., sharp or blunt), a cutting instrument, a tap, a screw, etc. The cutting instrument may be, or example, a drill, saw blade, burr, reamer, mill, scalpel blade, or any other implement that could cut bone or other tissue and is appropriate for use in a given operation.

In some embodiments, the navigation array 112 may be attached to the robotic connector (e.g., end effector 120, such as to an exterior surface of the guide tube) and may be described as a Robotic array (R-array), as will be discussed in greater detail with respect to FIG. 3. A complementary Small array 124 (e.g., an S-array) is attached to both the R-array (e.g., navigation array 112) and the tool 122. The R-array (e.g., navigation array 112) may have a universal fit shape with a plurality of mounting points 112a for fiducials and the S-array 124. The S-array 124 may, in some embodiments, be one of a plurality of relatively smaller arrays, each with a specific shape to be used with a predetermined tool, such as to achieve a proper depth or some other characteristic for the associated tool. For example, the R-array may exhibit high precision and define the trajectory, and the S-array may be of relatively lower accuracy and define a single point (such as a tip of an instrument) which is projected on the trajectory of the R-Array (e.g., for depth perception). In some embodiments, the R-array is attached to a coupling (FIG. 3). The individual S-arrays may be attached to instruments, at such points configured for the predetermined tool (e.g., for depth perception (e.g., pursuant to a Drill, Tap, Screw procedure)). In some embodiments, the R-array (attached to a robot arm) may return to a former position (as determined by the controller 106) while various S-arrays may be in different positions, e.g., a position appropriate for the predetermined tool.

Figure 2:
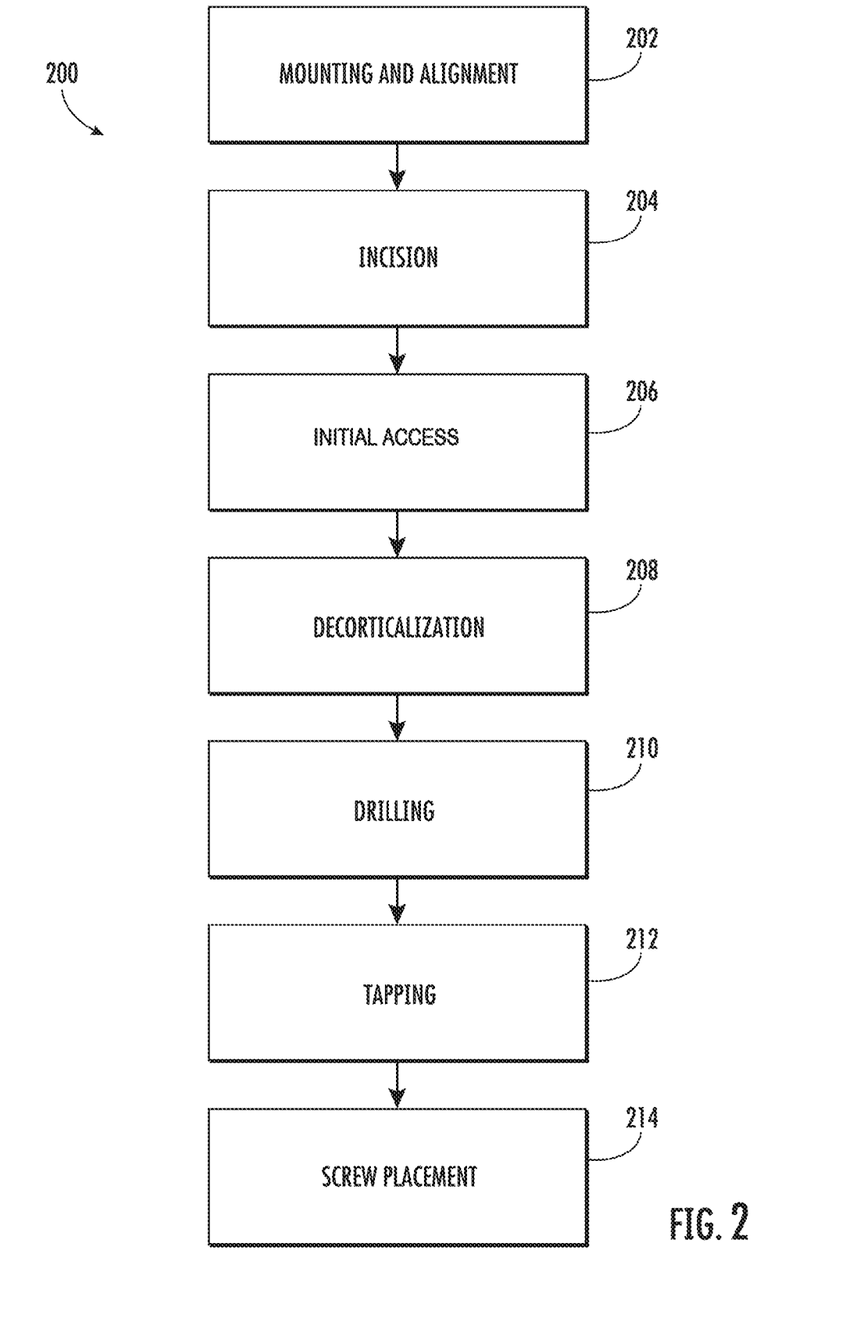
FIG. 2 shows a workflow for a surgical procedure which employs a computer-assisted surgical system.

FIG. 2 shows a workflow 200 for a surgical procedure (e.g., pursuant to a treatment plan) which may be employed with a computer-assisted surgical system (e.g., such as the computer-assisted surgical system of FIG. 1) having a robot arm, a controller, and a navigational system. For example, the surgical procedure may involve a patient's spine, such as placement of a screw in one or more pedicles of a patient's vertebrae. By way of a non-limiting example, the surgical procedure may employ a drill, tap, and screw technique, such as may be required as part of a transforaminal lumbar interbody fusion (TLIF) procedure. A series of tools may be required by the surgical procedure. One example of a procedure is a posterior pedicle screw placement for posterior stabilization which is often performed together with an interbody procedure (e.g., placement of a cage).

At step 202, an end effector, e.g., having a connector or coupler, that is adapted to receive a plurality of tools (e.g., different tools sequentially) is attached or mounted to a robot arm of a computer-assisted surgical system. In one example, the end effector (e.g., connector) is connected to an active robot arm. In one example, a passive arm receives an active end effector which is connected to the end effector (e.g., connector). The end effector may be coupled to the robot arm, for example, via an end plate locked by a lever. The end effector may have features for removably retaining a tool. The tool may be placed in a guide tube or other feature of the end effector and locked in the end effector via a locking mechanism such as a slider. In some embodiments, the end effector is adapted to be used with a Universal Navigation Adaptor Set (UNAS). An R-array equipped with fiducials may be mounted to the end effector, for example, on an outer ring defined on the guide tube.

Navigational assessments using a controller and associated navigational system may be performed to ensure alignment of the end effector. The alignment step may be performed with no tool in the end effector, with a referencing tool in the end effector, or with the first tool of the surgical procedure in the end effector. In some embodiments, the robot arm is only aligned once to the preplanned trajectory (for example, per pedicle screw insertion procedure). With respect to the arm and end effector, mounting may only need to be performed once, but with respect to a tool in the surgical procedure (e.g., each tool in the surgical procedure), the mounting and alignment step may be repeated at each tool change and/or distal tip change. A common reason for realignment is a detected deviation from a planned trajectory due to applied forces on the robotic system.

At step 204, a tool (e.g., such as a scalpel) retaining a cutting instrument (e.g., such as a scalpel blade) is placed in the end effector and locked in place. As will later be described, a scalpel guide may be placed in the connector to guide a scalpel holder (e.g., with blade) and therefore allow an opening of the patient in the exact trajectory given by the aligned (based on pre-planning) connector. Optionally, step 202 may be performed with respect to alignment of the tool (e.g., at a desired trajectory, position, and/or orientation). The robot arm may navigate to a starting position (a system with an active robot arm) or may be guided to the starting position (a system with a passive arm with an active end effector) by a user (e.g., a surgeon). The navigational system may store the position (e.g., a three-dimensional position). A cutting trajectory may be displayed on a display, along with imaging of the patient anatomy, etc. An incision is made in the patient to access the work site. The incision may be made manually by the surgeon. The incision may be made semi-autonomously, that is, controlled with at least partial robotic control (e.g., force assist from a robot, robotic constraint against movement beyond certain bounds or in certain planes while otherwise providing for manual control, determining to keep on a straight line, depth control, etc.). The incision may be made fully autonomously (e.g., controlled entirely by the controller). Once the incision is complete, the work site, such as a bone surface, is accessible. The navigational system may store a position (e.g., a three-dimensional position) of the robot arm and/or the end effector. For example, this position may include an incision boundary, or an incision depth determination. The tool may be removed from the end effector.

At step 206, a tool (e.g., such as a dilator) retaining a cutting instrument (e.g., such as a sharp dilator tip (or, alternatively, a blunt dilator tip)) is placed in the end effector and locked in place. This allows for initial access to the work site. Optionally, step 202 may be performed with respect to alignment of the tool (e.g., at a desired trajectory, position, and/or orientation). For example, the robot arm (and hence end effector), may be returned to a stored position. Imaging of the patient anatomy may be displayed on the display. The tool is inserted into the patient to access the work site. Control of the tool may be made manually, semi-autonomously, or fully autonomously, as described previously. In some embodiments, the initial access is a dilation procedure. Once the dilation procedure is complete, the navigational system may store a position (e.g., a three-dimensional position) of the robot arm and/or the end effector. For example, this position may include a depth determination that indicates a position of the bone surface. The tool may be removed from the end effector.

At step 208, a tool (e.g., such as for driving a burr) retaining a cutting instrument (e.g., such as a burr) is placed in the end effector and locked in place. The burr may be one of a variety of shapes, e.g., flat, round, or geometrical, with geometrical or non-geometrical cutting structures. Moreover, the burr may have a variety of configurations, e.g., fluted or non-fluted. Fluted burrs may have different numbers of cutting flutes. Optionally, step 202 may be performed with respect to alignment of the tool (e.g., at a desired trajectory, position, and/or orientation). For example, the robot arm (and hence end effector), may be moved such that the cutting instrument arrives at a stored position (e.g., a position on a bone surface). Imaging of the patient anatomy may be displayed on the display. The burr is inserted into the patient to access the work site and create a flat or other feature on the bone surface. The robot arm may move to achieve a predetermined trajectory. Control of the rotary tool driving the burr may be made manually, semi-autonomously, or fully autonomously, as described previously. Once the decorticalization procedure is complete, the navigational system may store a position (e.g., a three-dimensional position) of the robot arm and/or the end effector. For example, this position may include a depth determination that indicates a position and/or contour of the decorticalized bone surface. The tool may be removed from the end effector. As may be appreciated, in some embodiments, this step may be omitted depending on the type of screw to be installed.

At step 210, a tool (e.g., such as for driving a drill bit) retaining a cutting instrument (e.g., such as a drill bit) is placed in the end effector and retained in place. The drill bit may be one of a variety of diameters, lengths, and/or configurations, e.g., fluted or non-fluted. Optionally, step 202 may be performed with respect to alignment of the tool (e.g., at a desired trajectory, position, and/or orientation). For example, the robot arm (and hence end effector), may be moved such that the cutting instrument arrives at a stored position (e.g., a position on a bone surface). Imaging of the patient anatomy may be displayed on the display. The drill bit is inserted into the patient to access the work site and create a bore in the bone. The robot arm may move to achieve a predetermined trajectory. Control of the rotary tool driving the drill bit may be made manually, semi-autonomously, or fully autonomously, as described previously. Once the drilling procedure is complete, the navigational system may store a position (e.g., a three-dimensional position) of the robot arm and/or the end effector. For example, this position may include a depth determination that indicates a position of the bore. The tool may be removed from the end effector. As may be appreciated, in some embodiments, this step may be omitted depending on the type of screw to be installed.

At step 212, a tool (e.g., such as for driving a tap) retaining a cutting instrument (e.g., such as a tap) is placed in the end effector and locked in place. The tap may be selected based on a predetermined screw size (e.g., to be inserted into the bore at step 214). Optionally, step 202 may be performed with respect to alignment of the tool (e.g., at a desired trajectory, position, and/or orientation). For example, the robot arm (and hence end effector), may be moved such that the cutting instrument arrives at a stored position (e.g., a position on a bone surface). Imaging of the patient anatomy may be displayed on the display. The tap is inserted into the patient to access the work site and create threads in the bore in the bone. The robot arm may move to achieve a predetermined trajectory. Control of the rotary tool driving the tap may be made manually, semi-autonomously, or fully autonomously, as described previously. Once the tapping procedure is complete, the navigational system may store a position (e.g., a three-dimensional position) of the robot arm and/or the end effector. For example, this position may include a depth determination that indicates a position of the tapped bore. The tool may be removed from the end effector. As may be appreciated, in some embodiments, this step may be omitted depending on the type of screw to be installed.

At step 214, a tool (e.g., such as for driving a screw) retaining a cutting instrument (e.g., such as a screw) is placed in the end effector and locked in place. The screw may be a pedicle screw of a predetermined screw size (e.g., to be inserted into the tapped bore). Optionally, step 202 may be performed with respect to alignment of the tool (e.g., at a desired trajectory, position, and/or orientation). For example, the robot arm (and hence end effector), may be moved such that the cutting instrument arrives at a stored position (e.g., a position on a bone surface). Imaging of the patient anatomy may be displayed on the display. The screw is inserted into the patient to access the work site and be installed in the bore in the bone. The robot arm may move to achieve a predetermined trajectory. Control of the rotary tool driving the screw may be made manually, semi-autonomously, or fully autonomously, as described previously. Once the screw installation procedure is complete, the navigational system may store a position (e.g., a three-dimensional position) of the robot arm and/or the end effector. For example, this position may include a placement determination that indicates a position of the pedicle screw. The tool may be removed from the end effector.

FIG. 3 shows a schematic of a surgical workflow 300 where a single end effector 302 (e.g., connector) is adapted to retain a plurality of tools, such as may be used (e.g., sequentially) in the workflow. The workflow 300 may be similar to that described with respect to FIG. 2, and may be pursuant to a treatment plan. The workflow 300 may involve a patient's spine, such as placement of a screw in one or more pedicles of a patient's vertebrae. By way of a non-limiting example, the workflow 300 may employ a drill, tap, and screw technique, such as may be required as part of a transforaminal lumbar interbody fusion (TLIF) procedure. A series of tools may be required by the workflow 300, as will be described, represented by a series of figures. The series of figures share the same reference numerals where applicable, and, in some embodiments, the entire workflow 300 may be performed without changing end effectors. Advantageously, the bracketed central figures may be performed with an access guide which facilitates pedicle screw preparation.

The end effector 302 may be coupled to a robot arm (not depicted) such as, for example the robot arm 104 of FIG. 1, which may be part of a computer-assisted surgical system (e.g., such as the computer-assisted surgical system of FIG. 1) having the robot arm, a controller, and a navigational system. Embodiments with an active robot arm coupled to the end effector 302 and a passive arm with an active end effector coupled to the end effector 302 are contemplated. Navigational assessments using the controller and the navigational system may be performed to ensure alignment of the end effector 302. The alignment step may be performed with no tool in the end effector, with a referencing tool in the end effector, or with the first tool of the surgical procedure in the end effector.

The end effector 302 comprises an end plate 304 that is adapted to connect to a distal end of the robot arm (e.g., For example, the end plate 304 may be locked to the distal end of the robot arm by a spring loaded lever 306. Spaced apart from the end plate 304, the end effector 302 has a guide tube 308 for receiving a tool, as will be described. The guide tube 308 defines an aperture for receiving the tool and the aperture defines an axis which is shared by the tool (e.g., once the tool is retained in the guide tube). In some embodiments, an exterior surface of the guide tube 308 defines a ring for attaching a navigation array, as will be described. The end effector 302 also comprises a slider (e.g., locking mechanism) 310 for locking the tool in the guide tube 308. In some embodiments, the slider 310 includes a lever 312 for engaging or disengaging the slider. After use of the tool, the slider 310 may be disengaged, such as to remove the tool, and thus, the end effector 302 is said to removably retain the tool. Other locking mechanisms are contemplated.

An array ring 314 may be attached to the end effector 302, such as to an exterior surface of the guide tube 308. The array ring 314 is attached to a navigation array 316 (e.g., an R-array). The R-array 316 may have a universal fit shape with a plurality of mounting points 318 for fiducials (not depicted). An S-array, such as S-array 120 (second from the left in FIG. 3), may slide in a notch within the R-array (e.g., the S-array is mounted on an instrument to provide depth perception). As will be described, individual S-arrays may have points configured for the predetermined tool, for example, to achieve a certain depth. In some embodiments, this allows the R-array 316 to return to a former position (as determined by the controller) while a subsequent S-array may be in a completely different position from the former S-array, but a position appropriate for the predetermined tool.

Turning to the far left of FIG. 3, a scalpel 322 is removably retained by the end effector 302. In some embodiments, the scalpel 322 is placed in a scalpel guide (not depicted) which has an inner opening (e.g., a bore, a slot, etc.) adapted to receive the scalpel and an outer surface with a diameter that is predetermined to correspond to an inner diameter of the guide tube 308. Engaging the slider 310 locks the scalpel guide, and hence, scalpel 322 in place in the guide tube 308. The scalpel 322 has a scalpel blade 322a (e.g., a cutting instrument) at its distal end and a handle 324 at its proximal end.

The scalpel 322 may be aligned (e.g., at a desired trajectory, position, and/or orientation). The robot arm (not depicted) may navigate to a starting position or may be guided to the starting position by a user (e.g., a surgeon). The navigational system (not depicted) may store the position (e.g., a three-dimensional position). A cutting trajectory may be displayed on a display (not depicted), along with imaging of the patient anatomy, etc. An incision is made in the patient to access the work site. The incision may be made manually by the surgeon. The incision may be made semi-autonomously, that is, controlled with at least partial robotic control (e.g., force assist from a robot, robotic constraint against movement beyond certain bounds or in certain planes while otherwise providing for manual control, determining to keep on a straight line, depth control, etc.). The incision may be made fully autonomously (e.g., controlled entirely by the controller). Once the incision is complete, the work site, such as a bone surface, is accessible. The navigational system may store a position (e.g., a three-dimensional position) of the robot arm and/or the end effector 302. For example, this position may include an incision boundary, or an incision depth determination. The scalpel 322 may be removed from the end effector 302.

Moving right in FIG. 3, the S-array 320 is attached to an initial access tool 328. The S-array 320 may have unique geometry and/or mounting points adapted to correspond to the initial access tool 328. For example, the S-array 320 be one of a plurality of relatively smaller arrays, each with a specific shape to be used with a predetermined tool, such as to achieve a proper depth or some other characteristic for the associated tool.

The initial access tool 328 is removably retained by the end effector 302. As will be described in greater detail in FIGS. 4A-6C, the initial access tool 328 is part of a modular system that is highly adaptable (for example, to accommodate a surgeon's preferences for this step of, for example, of a pedicle screw placement workflow. The initial access tool 328 has a distal tip 328a that may be a sharp tip, a blunt tip, a relatively large diameter tip, a retractable tip, or a rigid tip.

Preferably, the initial access tool 328 engages an access guide 330, such as by a clip (or a button), and the access guide is removably retained by the guide tube 308. Engaging the slider 310 locks the access guide 330 in place in the guide tube 308.

The initial access tool 328 may be aligned (e.g., at a desired trajectory, position, and/or orientation). The robot arm may navigate to a starting position or may be guided to the starting position by a user (e.g., a surgeon). The navigational system may store the position (e.g., a three-dimensional position). An axis trajectory may be displayed on a display, along with imaging of the patient anatomy, etc. Access to the work site may be made manually by the surgeon, semi-autonomously as described above, or fully autonomously (e.g., controlled entirely by the controller). The navigational system may store a position (e.g., a three-dimensional position) of the robot arm, the end effector 302, the initial access tool 328, or the distal tip 328a. For example, this position may include a depth determination that indicates a position and/or contour of the bone surface. Measurements may be taken and stored. The initial access tool 328 may be removed from the access guide 330 (e.g., while the access guide is retained by the end effector 302).

Moving right in FIG. 3, the access guide 330 receives and retains a burr tool 332. For example, the burr tool 332 may have a twist lock to engage a corresponding feature of the access guide 330. The burr tool 332 has a distal burr 332a. The burr 332a may be one of a variety of shapes, e.g., flat, round, or geometrical with geometrical or non-geometrical cutting structures. Moreover, the burr 332a may have a variety of configurations, e.g., fluted or non-fluted. Fluted burrs may have different numbers of cutting flutes.

The burr tool 332 may be guided (e.g., at a desired trajectory, position, and/or orientation). The robot arm may navigate to a starting position or may be guided to the starting position (e.g., pursuant to the pre-planned trajectory) by a user (e.g., a surgeon). The navigational system may store the position (e.g., a three-dimensional position) and/or may compare the position to a previously stored position (e.g., to determine how to move the robot arm such that the burr 332a arrives at a stored position (e.g., a position on a bone surface)). An axis trajectory may be displayed on a display, along with imaging of the patient anatomy, etc. The burr 332a may be used to create a flat or other feature on the bone surface. Control of the burr tool 332 may be performed manually by the surgeon, semi-autonomously as described above, or fully autonomously (e.g., controlled entirely by the controller). The navigational system may store a position (e.g., a three-dimensional position) of the robot arm, the end effector 302, the burr tool 332, or the burr 332a. For example, this position may include a depth determination that indicates a position and/or contour of the bone surface. Measurements may be taken and stored. The burr tool 332 may be removed from the access guide 330 (e.g., while the access guide is retained by the end effector 302).

Moving right in FIG. 3, a navigation sleeve 333 engages a drill tool 334 at a first end and an S-array 335 at a second end. The S-array 335 has a specific shape to be used with a predetermined tool (e.g., in this case, the drill tool 334) such as to achieve a proper depth or some other characteristic for the associated tool (e.g., the shape enables the navigation system to identify the instrument which is in use). The navigation sleeve 333 is adapted to allow the drill tool 334 to rotate, such as when attached to a rotary tool (not depicted). In some embodiments, the navigation sleeve 333 is part of a Universal Navigation Adaptor Set (UNAS) and is a rotating adaptor. The navigation sleeve 333 provides the ability to mount an array on a rotating instrument to allow the instrument navigation/depth perception (e.g., to allow the drill tool 334 to maintain a predetermined trajectory).

The access guide 330 receives and retains the drill tool 334. For example, the drill tool 334 may have a twist lock to engage a corresponding feature of the access guide 330. The drill tool 334 has a distal drill bit 334a. The drill bit 334a may be one of a variety of diameters, lengths, and/or configurations, e.g., fluted or non-fluted. The drill tool 334 may be aligned (e.g., at a desired trajectory, position, and/or orientation) by the robot arm, but also is aligned by the end effector 302 and its guiding channel. The robot arm may navigate to a starting position or may be guided to the starting position by a user (e.g., a surgeon). The navigational system may store the position (e.g., a three-dimensional position) and/or may compare the position to a previously stored position (e.g., to determine how to move the robot arm such that the drill bit 334a arrives at a stored position (e.g., a position on a bone surface)). An axis trajectory may be displayed on a display, along with imaging of the patient anatomy, etc. The drill bit 334a may be used to create a bore in the bone. Control of the drill tool 334 may be performed manually by the surgeon, semi-autonomously as described above, or fully autonomously (e.g., controlled entirely by the controller). The navigational system may store a position (e.g., a three-dimensional position) of the robot arm, the end effector 302, the drill tool 334, or the drill bit 334a. For example, this position may include a depth determination that indicates a position or trajectory of the bore. Measurements may be taken and stored. The drill tool 334 may be removed from the access guide 330 (e.g., while the access guide is retained by the end effector 302).

Moving right in FIG. 3, the navigation sleeve 333 engages a tapping tool 338 at a first end and an S-array 337 at a second end. The S-array 337 has a specific shape to be used with a predetermined tool (e.g., in this case, the tapping tool 338) such as to achieve a proper depth or some other characteristic for the associated tool. The navigation sleeve 333 is adapted to allow the tapping tool 338 to rotate, such as when attached to a rotary tool or other driver (not depicted). In some embodiments, the navigation sleeve 333 is part of a Universal Navigation Adaptor Set (UNAS) and is a rotating adaptor.

The access guide 330 receives and retains the tapping tool 338. The tapping tool 338 has a distal tap 338a (e.g., to be inserted into the bore created by the drill bit 334a). The tap 338a may be selected based on a predetermined screw size. The navigational system may store the position (e.g., a three-dimensional position) and/or may compare the position to a previously stored position (e.g., to determine how to move the robot arm such that the tap 338a arrives at a stored position (e.g., the bore)). An axis trajectory may be displayed on a display, along with imaging of the patient anatomy, etc. The tap 338a may be used to contour the bone. Control of the tapping tool 338 may be performed manually by the surgeon, semi-autonomously as described above, or fully autonomously (e.g., controlled entirely by the controller). The navigational system may store a position (e.g., a three-dimensional position) of the robot arm, the end effector 302, the tapping tool 338, or the tap 338a. For example, this position may include a depth and/or trajectory determination that indicates a position of the tapped bore. Measurements may be taken and stored. The tapping tool 338 and the access guide 330 may be removed from the end effector 302.

Moving right in FIG. 3, the navigation sleeve 333 engages a driver 340 at a first end and an S-array 339 at a second end. The S-array 339 has a specific shape to be used with a predetermined tool (e.g., in this case, the driver 340) such as to achieve a proper depth or identify the associated tool to the navigation system. In some embodiments, the navigation sleeve 333 is part of a Universal Navigation Adaptor Set (UNAS) and is a rotating adaptor.

The driver 340 is placed in the end effector 302. The driver 340 is adapted to retain and drive a pedicle screw 340a of a predetermined screw size (e.g., to be inserted into the tapped bore). The driver 340 may be moved to a starting position or may be guided to the starting position by a user (e.g., a surgeon). The navigational system may store the position (e.g., a three-dimensional position) and/or may compare the position to a previously stored position (e.g., to determine how to move the robot arm such that the pedicle screw 340a arrives at a stored position (e.g., the tapped bore)). An axis trajectory may be displayed on a display, along with imaging of the patient anatomy, etc. The screw 340a is inserted into the bore in the bone (e.g., burring, drilling, tapping, and combinations thereof may be optionally varied depending on screw geometry and surgeon preference). Control of the rotary tool driving the screw may be made manually, semi-autonomously, or fully autonomously, as described previously. The navigational system may store a position (e.g., a three-dimensional position) of the robot arm, the end effector 302, the driver 340, or the screw 340a. For example, this position may include a depth and/or trajectory determination that indicates a position of the screw 340a. Measurements may be taken and stored. The driver 340 may be removed from the end effector 302.

Figure 4A:
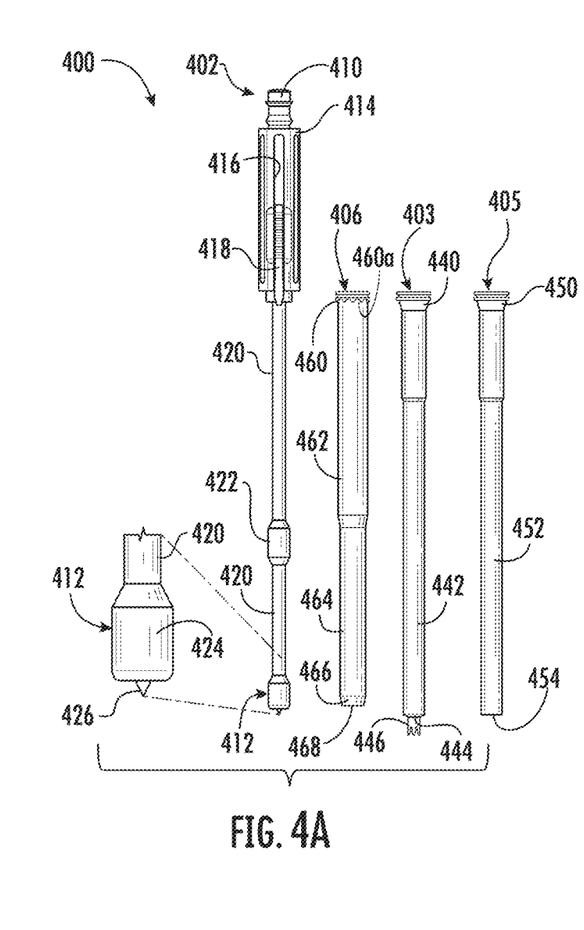
FIG. 4A shows a group of tool components according to one embodiment including a detail view.

FIG. 4A shows a group 400 of tool components, for example, for selection and combination to set up an initial access tool 402 (such as, for example, the initial access tool 328 (FIG. 3)) for disposing in an access guide 406 (such as, for example, the access guide 330 (FIG. 3)). Also provided in the group are a first guide 403 and a second guide 405, as will be described.

The initial access tool 402 has a proximal end 410 and a distal end 412. A housing 414 is disposed adjacent to the proximal end 410, the housing defining a plurality of openings 416. A locking button 418 (e.g., a lever with an axis) is disposed in one of the openings 416. Although not visible in the figure, another locking button (e.g., substantially similar to the locking button 418) may be disposed on an opposing side of the housing 414. In operation, the locking button 418 detachably engages a proximal end of the access guide 406 to detachably connect the initial access tool 402 to the access guide (FIG. 4C). A shaft 420 extends from the housing 414 to the distal end 412. A step portion 422 of the shaft 420 has a greater diameter than the shaft. Referring to the detail view, the distal end 412 comprises another step portion 424 having a greater diameter than the shaft 420 and an indexing point 426 disposed in the center of the step portion, coaxial to the shaft. In some embodiments, the step portion 424 has a rounded distal edge.

The first guide 403 comprises a proximal end 440 and a hollow guide portion 442 extending from the proximal end and terminating in a distal end 444. An annular toothed portion 446 extends from the distal end 444 to engage a bone surface.

The second guide 405 comprises a proximal end 450 and a hollow guide portion 452 extending from the proximal end and terminating in a distal end 454. The hollow guide portion 452 may have an internal diameter approximately the same as the hollow guide portion 442 (e.g., of first guide 403). However, as can be appreciated, an opening of the second guide 405 at the distal end 545 has a relatively larger diameter than an opening of the first guide 403 at the distal end 444 (e.g., the opening also passing through the toothed portion 446).

The access guide 406 comprises a proximal end 460 having a plurality of indents 460a, a first hollow guide portion 462 extending from the proximal end, and a reduced diameter second hollow guide portion 464 extending from the first hollow guide portion. A chamfer 466 is disposed at a distal end 468 of the second hollow guide portion 464, for example to prevent tissue damage as the access guide is inserted into an incision in a patient. The second hollow guide portion 464 has an internal diameter that is greater than an outer diameter of either the hollow guide portion 442 (e.g., of first guide 403) or the hollow guide portion 452 (e.g., of the second guide 405).

Figure 4B:
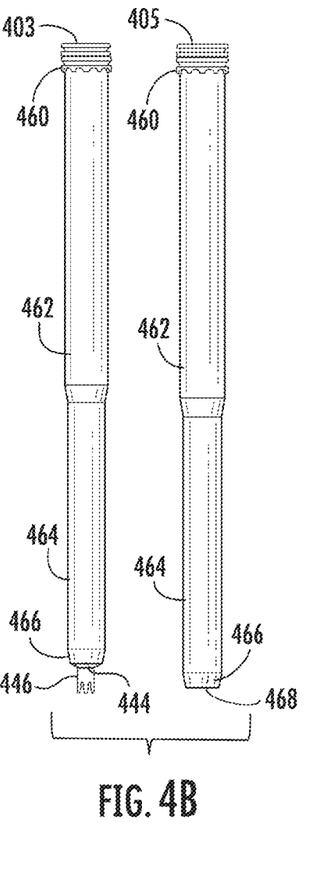
FIG. 4B shows a pair of alternate sub-assemblies from the group of FIG. 4A.
Figure 4C:
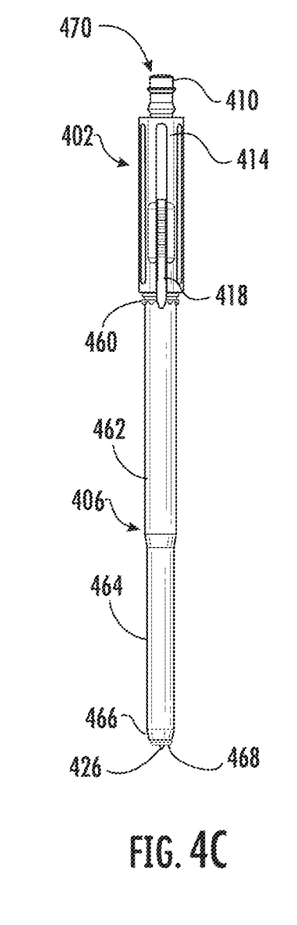
FIG. 4C shows a tool assembled from a portion of the group of FIG. 4A.

FIG. 4B shows a pair of alternate sub-assemblies comprising the first guide 403 nested in the access guide 406 (left in FIG. 4B) and the second guide 405 nested in the access guide (right in FIG. 4B).

In some embodiments, an initial access tool (such as the initial access tool 328 (FIG. 3)) may extend through the first guide 403 and the access guide 406. In some embodiments, a drill tool (such as the drill tool 334 (FIG. 3)) may extend through the first guide 403 and the access guide 406. If access guide 406 is retained in the end effector (e.g., connector), the first guide 403 may be adapted to prevent rotation between the first guide and the access guide 406, for example, to prevent bone damage by rotation of the toothed portion 446. Features of the proximal end 440 may cooperate with features of the proximal end 460 to prevent rotation.

In some embodiments, an initial access tool (such as the initial access tool 328 (FIG. 3)) may extend through the second guide 405 and the access guide 406. In some embodiments, a burr tool (such as the burr tool 332 (FIG. 3)) may extend through the second guide 405 and the access guide 406. The second guide 405 may rotate freely in the access guide 406 or alternatively, features of the proximal end 450 may cooperate with features of the proximal end 460 to prevent rotation.

FIG. 4C shows an assembled instrument 470 comprising the initial access tool 402 detachably connected to the access guide 406. In some embodiments, the second guide 405 (not visible) is present. The locking button 418 detachably engages the proximal end 460 of the access guide 406 (e.g., engaging one of the plurality of indents 460a). Accordingly, the locking button 418 prevents rotation of the access guide 406 with respect to the housing 414. The shaft 420 (not visible) extends through the first hollow guide portion 462 and the second hollow guide portion 464. The step portion 424 and the indexing point 426 protrude from the distal end 468 adjacent the chamfer 466. Tolerances between the outer diameter of the step portion 424 and the inner diameter of the distal end 468 may be tight to avoid tissue being caught in a gap between the step portion and distal end.

Figure 5A:
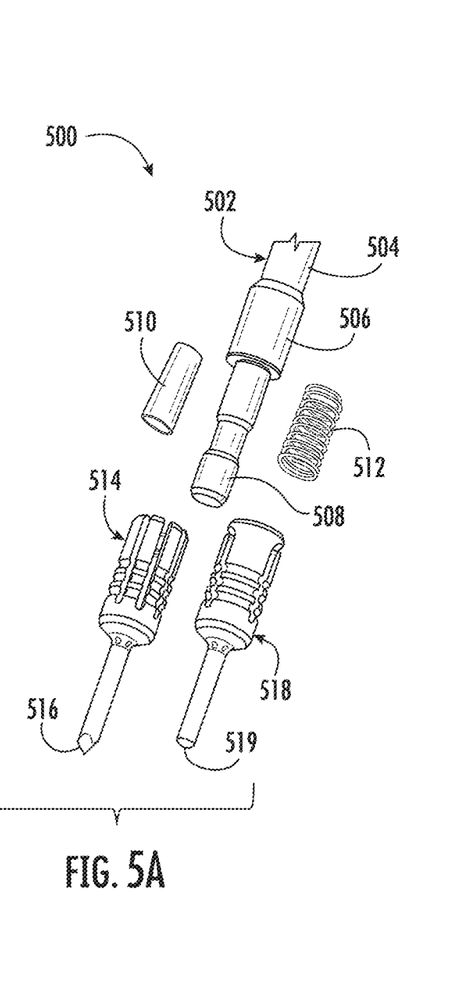
FIG. 5A shows a distal enlarged view of a group of tool components according to another embodiment.

FIG. 5A shows a distal enlarged view of a group 500 of tool components for selection and combination to set up an initial access tool 502 (such as, for example, the initial access tool 328 (FIG. 3)). A shaft 504 of the initial access tool 502 has a step portion 506 having a greater diameter than the shaft. A distal end 508 of the shaft 504 may retain either a rigid sleeve 510 or a spring 512, both of which have an inner diameter sufficient to pass over the outer diameter of the distal end. A first exchangeable tip 514 is adapted to engage the distal end 508. The tip 514 has a sharp tip 516. A second exchangeable tip 518 is also adapted to engage the distal end 508. The tip 518 has a blunt tip 519. As can be appreciated, a surgeon can select the rigid sleeve 510, the spring 512, the tip 514, and the tip 519 to achieve a desired distal tip of the initial access tool 502, for example, a rigid sharp tip, a retractable sharp tip, a rigid blunt tip, or a retractable blunt tip.

Figures 5B, 5C:
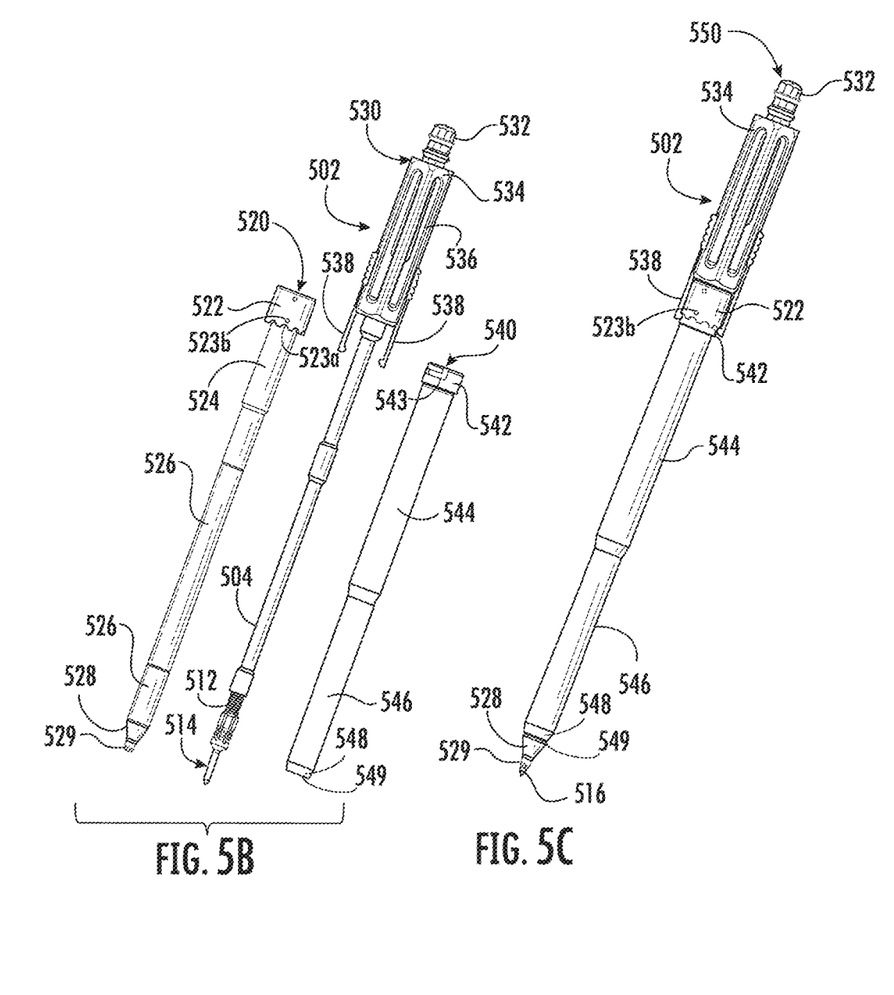
FIG. 5B shows an exploded view of a tool assembled from a portion of the group of FIG. 5A.
FIG. 5C shows the assembled tool of FIG. 5B.

FIG. 5B shows a guide 520 comprising a proximal end 522 having a plurality of indents 523a and at least one pin 523b, a first hollow guide portion 524 extending from the proximal end, a second hollow guide portion 526 extending from the first hollow guide portion, a chamfered portion 528 extending from the second hollow guide portion, and an annular toothed portion 529 at a distal end to engage a bone surface. In some embodiments, the guide 520 may be similar to the first guide 403 (FIG. 4).

The initial access tool 502 further comprises a proximal portion 530 comprising a proximal end 532 and a housing 534 adjacent to the proximal end. The housing 534 defines a plurality of openings 536. A pair of locking buttons 538 are slidably disposed in corresponding openings 536. In operation, the locking buttons 538 detachably engage features of the proximal end 522 (of the guide 520), such as corresponding indents of the plurality of indents 523a, to detachably connect the initial access tool 502 to the guide 520 (FIG. 5C). As depicted, the spring 512 and the exchangeable tip 514 have been selected and placed over the distal end 508 of the shaft 504 to afford a sharp retractable tip.

An access guide 540 comprises a proximal end 542 having an L-shaped slot 543, a first hollow guide portion 544 extending from the proximal end, and a reduced diameter second hollow guide portion 546 extending from the first hollow guide portion. A chamfer 548 is disposed at a distal end 549 of the second hollow guide portion 546, for example to prevent tissue damage as the access guide is inserted into an incision in a patient. The second hollow guide portion 546 has an internal diameter that is greater than an outer diameter of the hollow guide portion 526.

FIG. 5C shows an assembled instrument 550 comprising the initial access tool 502 detachably connected to the guide 520 and, in turn, the guide detachably connected to the access guide 540. The locking buttons 538 detachably engage corresponding indents of the plurality of indents 523a (of the proximal end 522). The guide 520 is disposed in the access guide 540 and detachably connected. For example, the pin 523b (of the guide proximal end 522) is placed in the slot 543 (of the access guide proximal end 542), and the access guide 540 rotated counterclockwise to lock the access guide to the guide 520. Accordingly, rotation of the access guide 540 with respect to the housing 534 is prevented.

The shaft 504 (not visible) extends through the hollow guide portions 524 and 526, and the sharp tip 516 protrudes from the chamfered portion 528 and the annular toothed portion 529. The chamfered portion 528 protrudes from the chamfer 548 disposed at the distal end 549 of the access guide 540. Tolerances between the outer diameter of the hollow guide portion 526 and the inner diameter of the distal end 549 may be tight to avoid tissue being caught in a gap between them. In some embodiments, the assembled instrument 550 may be used in a workflow with a drill step.

Figure 6A:
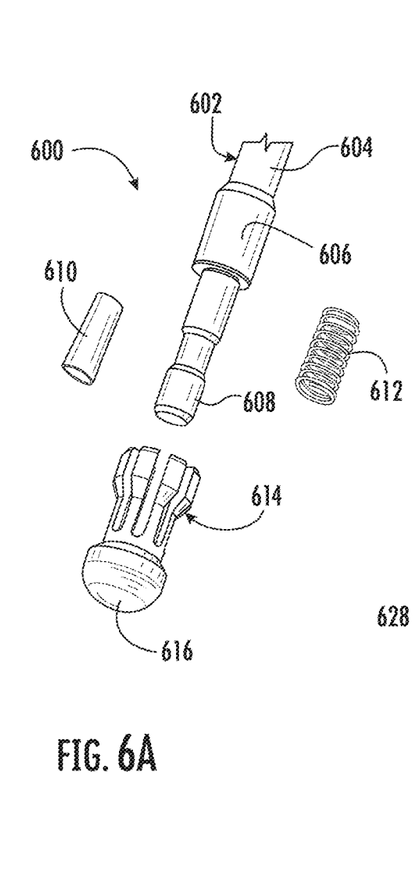
FIG. 6A shows a distal enlarged view of a group of tool components according to yet another embodiment.

FIG. 6A shows a distal enlarged view of a group 600 of tool components for selection and combination to set up an initial access tool 602 (such as, for example, the initial access tool 328 (FIG. 3)). A shaft 604 of the initial access tool 602 has a step portion 606 having a greater diameter than the shaft. A distal end 608 of the shaft 604 may retain either a rigid sleeve 610 or a spring 612, both of which have an inner diameter sufficient to pass over the outer diameter of the distal end. An exchangeable tip 614 is adapted to engage the distal end 608. The tip 614 has a blunt tip 616. As can be appreciated, a surgeon can select the rigid sleeve 610 or the spring 612, and the tip 614, to achieve a desired distal tip of the initial access tool 602, for example, a rigid blunt tip or a retractable blunt tip (FIG. 6B).

Figures 6B, 6C:
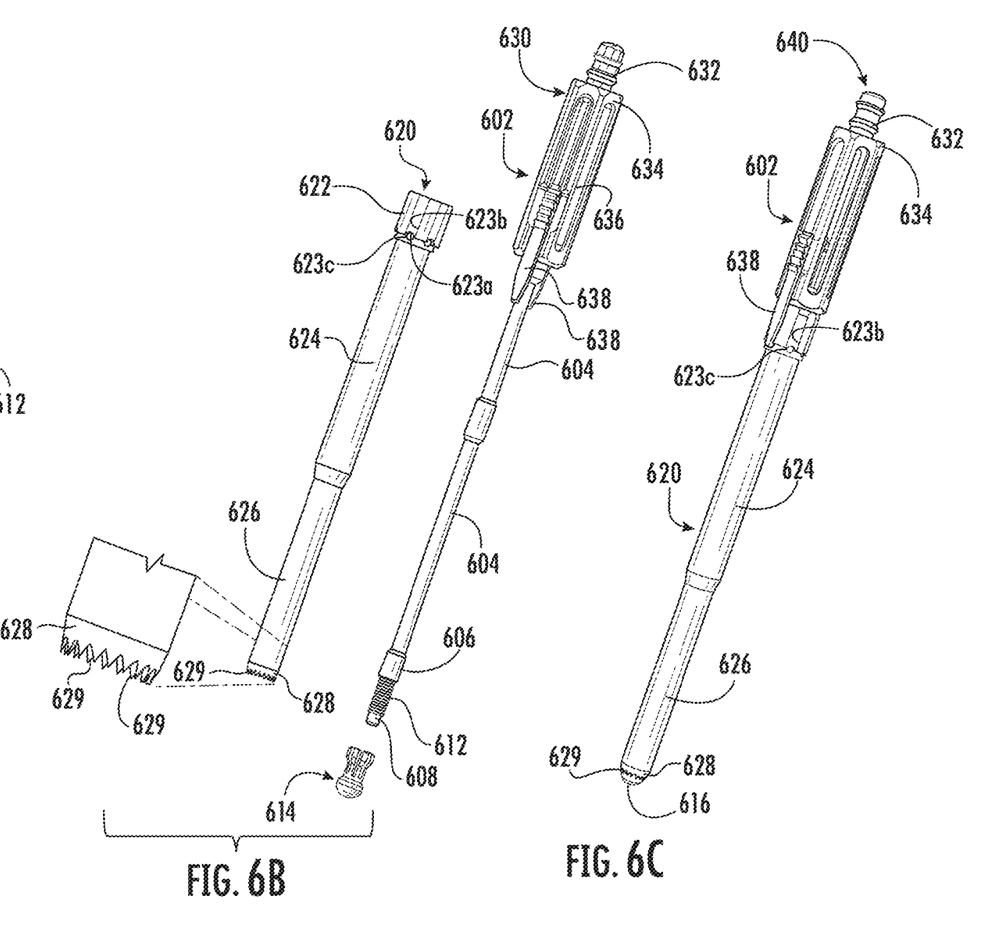
FIG. 6B shows an exploded view of a tool assembled from a portion of the group of FIG. 6A, including a detail view.
FIG. 6C shows the assembled tool of FIG. 6B.

FIG. 6B shows an access guide 620 comprising a proximal end 622 having a plurality of indents 623a. Each of the plurality of indents 623a may have an associated groove 623b (e.g., that leads to the indent). A recess 623c may be associated with each of the plurality of indents 623a. A first hollow guide portion 624 extends from the proximal end 622. A reduced diameter second hollow guide portion 626 extends from the first hollow guide portion 624. A chamfered portion 628 extends from the second hollow guide portion 626, for example to prevent tissue damage as the access guide is inserted into an incision in a patient. An annular toothed portion 629 (e.g., to engage a bone surface) is disposed at a distal end of the second hollow guide portion 626.

The initial access tool 602 further comprises a proximal portion 630 comprising a proximal end 632 and a housing 634 adjacent to the proximal end. The housing 634 defines a plurality of openings 636. A pair of locking buttons 638 are slidably disposed in corresponding openings 636. In operation, the locking buttons 638 detachably engage features of the proximal end 622 (of the access guide 620), such as corresponding indents of the plurality of indents 623a, to detachably connect the initial access tool 602 to the access guide 620 (FIG. 6C). For example, distal portions of the locking buttons 638, such as a boss (not visible) may slide down corresponding grooves 623b and come to rest in the indents 623a and recesses 623c of the access guide 620 (FIG. 6C). As depicted, the spring 612 and the exchangeable tip 614 have been selected and placed over the distal end 608 of the shaft 604 to afford a blunt retractable tip.

FIG. 6C shows an assembled instrument 640 comprising the initial access tool 602 detachably connected to the access guide 620. The locking buttons 638 detachably engage corresponding indents of the plurality of indents 623a (of the proximal end 622). Accordingly, the locking buttons 638 prevent rotation of the access guide 620 with respect to the housing 634.

The shaft 604 (not visible) extends through the hollow guide portions 624 and 626, and the blunt tip 616 protrudes from the chamfered portion 628 and the annular toothed portion 629. The chamfered portion 628 protrudes from the chamfer 648 disposed at the distal end 649 of the access guide 640. In some embodiments, tolerances between the annular toothed portion 629 and exchangeable tip 614 may be tight to avoid tissue being caught in a gap between them (e.g., to close the lumen of the access guide 620). The tip 614 may be retractable (due to the spring 612) to allow the annular toothed portion 629 of the access guide 620 to engage bone. In some embodiments, the assembled instrument 640 may be used in a workflow without a drill step.

Figure 7A:
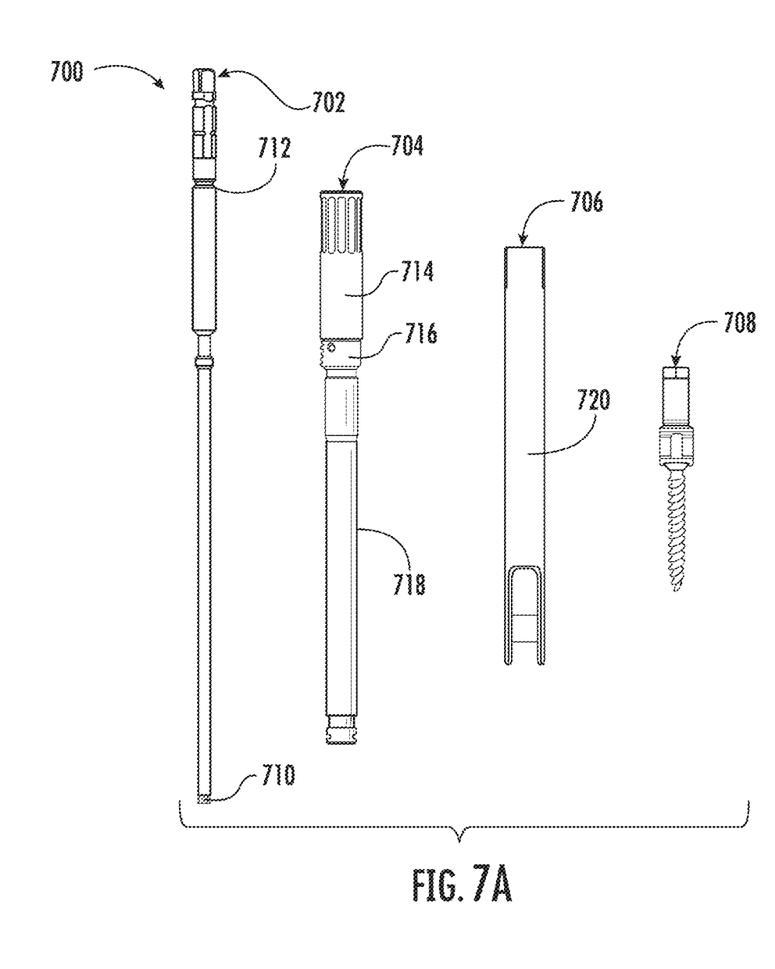
FIG. 7A shows an exploded view of a group of tool components according to yet another embodiment.

FIG. 7A shows a group 700 of tool components, for example, for selection and combination to set up a driver tool 702 (such as, for example, a driver 340 (FIG. 3). The driver 702 is adapted to be received in a guide 704. A second guide 706 is disposed over a distal portion of the guide 704. A pedicle screw 708 is adapted to be driven by the driver 702, such as by a distal tip 710. The driver 702 also retains a groove 712 to facilitate attachment of a navigation sleeve 713 (FIG. 7B), such as navigation sleeve 333 (FIG. 3), to the driver.

Figure 7B:
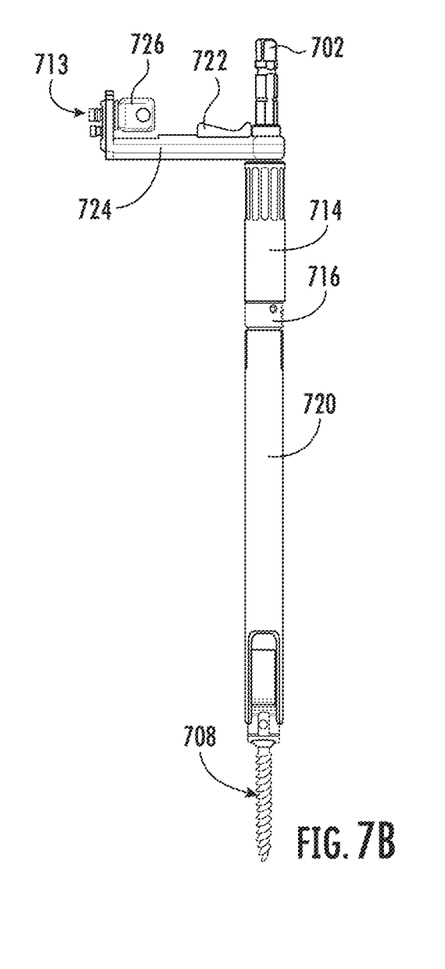
FIG. 7B shows the assembled tool of FIG. 7A disposed in a navigation sleeve.

The guide 704 comprises a thread locker 714, a ring locking mechanism 716, and a distal portion 718 adapted to be inserted into the guide 706. The guide 706 retains a guide spring (not visible) to engage the ring locking mechanism 716 to lock the guide to the guide 704. The guide 706 defines a hollow body 720, the hollow body surrounding a portion of the pedicle screw 708 in the assembled position (FIG. 7B).

The navigation sleeve 713 comprises a bore (not visible) for receiving the driver 702. A lock mechanism 722 is adapted to engage the groove 712, thereby allowing the driver 702 to rotate. An arm 724 of the navigation sleeve extends outward from the locking mechanism 722. An S-array attachment mechanism 726 is attached to the arm 724 for connecting the navigation sleeve to an S-array (such as, for example, S-array 339 (FIG. 3).

In operation, the pedicle screw 708 may be a specific type (e.g., thread arrangement, diameter, cannulation, approved use) that dictates the installation workflow. In some embodiments, the installation workflow comprises decorticalization, drilling, and tapping before installation of the pedicle screw 708. In some embodiments, the installation workflow comprises only decorticalization before installation of the pedicle screw 708. In some embodiments, the installation workflow comprises only drilling and tapping before installation of the pedicle screw 708. In some embodiments, the installation workflow comprises only drilling before installation of the pedicle screw 708.

As can be appreciated, the presently described embodiments may also be applicable to cervical procedures, etc.

Examples of the above-described embodiments may include the following.

In a first example, a robotic surgical system including a robotic arm is disclosed, the system comprising an end effector (e.g., connector) attached to the robotic arm and retaining an access guide, and an initial access tool detachably connected to the access guide, wherein the initial access tool comprises a housing, a shaft extending from the housing coaxially through the access guide, and a distal tip attached to the shaft and protruding from a portion of the access guide distal to the end effector, wherein the housing is adapted to prevent rotation with respect to the access guide. In some embodiments, the access guide is adapted to retain an initial access tool and one or more of a burring tool, a drilling tool, or a tapping tool. The tip may be a rigid blunt tip, a retractable blunt tip, a rigid generally blunt tip with a central indexing point, a rigid sharp tip, or a retractable sharp tip. The housing may retain a locking button for engaging the access guide. The locking button may be disposed in an opening in the housing. The access guide may have a plurality of indents in a portion of the access guide proximal to the end effector for engaging the locking button. The access guide may have a plurality of teeth disposed at an end distal to the end effector. The access guide may have a smooth chamfer disposed at an end distal to the end effector. The robotic surgical system may further comprise a second guide interposed between the shaft and the access guide. The housing may retain a locking button for engaging the access guide, trapping the second guide between the housing and the access guide. The housing may retain a locking button for engaging the second guide and preventing rotation with respect to the second guide. The second guide may have a plurality of indents in a portion of the second guide proximal to the end effector for engaging the locking button. The second guide may have a pin for engaging a slot of the access guide, thereby preventing rotation between the housing, the second guide, and the access guide. The second guide may have a plurality of teeth disposed at an end distal to the end effector. The robotic surgical system may further comprise a first array attached to the end effector and a second array attached to the initial access tool (e.g., between the first array and the initial access tool).

In a second example, a method comprises providing a robotic surgical system comprising a robotic arm, an end effector attached to the robotic arm and retaining an access guide, wherein the access guide is adapted to retain an initial access tool and one or more of a burring tool, a drilling tool, or a tapping tool, a navigational array attached to the end effector, and a controller configured to operate the robotic arm to position end effector, accessing a bone surface of a patient, contacting the bone surface with the initial access tool, and contacting the bone surface with the one or more of the burring tool, the drilling tool, or the tapping tool. In some embodiments, each of the burring tool, the drilling tool, and the tapping tool are used, and each are retained in the access guide in sequence.

In a third example, an instrument set for use with a robotic surgical system is provided, the set comprising an access guide, an initial access tool comprising a housing and a shaft extending from the housing and having a step spaced from a distal end of the shaft, a rigid sleeve for placing over the shaft below the step, a spring for placing over the shaft below the step, and at least one detachable tip for engaging the distal end of the shaft, wherein the housing is adapted to prevent rotation with respect to the access guide. The instrument set may further comprise a blunt detachable tip and a sharp detachable tip. The housing retain a locking button for engaging a plurality of indents in a proximal portion of the access guide. The access guide may have a plurality of teeth or a smooth chamfer disposed at distal end. The instrument set may further comprise a second guide for interposing between the shaft and the access guide. The second guide may have a plurality of teeth disposed at a distal end.

The invention claimed is:

1. A robotic surgical system including a robotic arm, the system comprising:
   an end effector attached to the robotic arm and retaining an access guide, the access guide comprising an end proximal to the end effector, the end having a plurality of spaced apart indents oriented axially on an outer surface of the access guide; and
   an initial access tool detachably connected to the access guide, wherein the initial access tool comprises:

a housing having a pair of locking buttons slidably disposed axially in an opening disposed in the housing, the locking buttons moving axially with respect to the tool between a first position and a second position wherein a distal boss portion of each of the locking buttons engages a respective one of the indents of the access guide radially inwardly to prevent rotation between the initial access tool and the access guide;

a shaft extending from the housing coaxially through the access guide; and a distal tip attached to the shaft and protruding from a portion of the access guide distal to the end effector.

2. The robotic surgical system of claim 1, wherein the tip is a rigid blunt tip, a retractable blunt tip, a rigid generally blunt tip with a central indexing point, a rigid sharp tip, or a retractable sharp tip.

3. The robotic surgical system of claim 1, wherein the access guide has a plurality of teeth disposed at the end distal to the end effector.

4. The robotic surgical system of claim 1, wherein the access guide has a smooth chamfer disposed at the end distal to the end effector.

5. The robotic surgical system of claim 1, further comprising a second guide interposed between the shaft and the access guide.

6. The robotic surgical system of claim 5, wherein the locking buttons engaging the indents of the access guide traps the second guide between the housing and the access guide.

7. The robotic surgical system of claim 5, wherein the locking buttons prevent rotation between the housing and the second guide.

8. The robotic surgical system of claim 7, wherein the second guide has a plurality of indents in a portion of the second guide proximal to the end effector for engaging the locking buttons.

9. The robotic surgical system of claim 5, wherein the second guide has a pin for engaging a slot of the access guide, thereby preventing rotation between the housing, the second guide, and the access guide.

10. The robotic surgical system of claim 5, wherein the second guide has a plurality of teeth disposed at an end distal to the end effector.

11. The robotic surgical system of claim 1, further comprising a first array attached to the end effector and a second array attached to the initial access tool.

12. A robotic surgical system including a robotic arm, the system comprising:

an end effector attached to the robotic arm;

a first array attached to the end effector;

an access guide retained by the end effector, the access guide comprising an end proximal to the end effector, the end having a plurality of spaced apart indents oriented axially on an outer surface of the access guide; and an initial access tool detachably connected to the access guide, wherein the initial access tool comprises:

a housing having an opening axially disposed in the housing;

a pair of locking buttons slidably disposed in the opening, the locking buttons moving axially with respect to the opening and the tool between a first position and a second position, wherein a distal boss portion of each of the locking buttons engages a respective one of the indents of the access guide radially inwardly to prevent rotation between the initial access tool and the access guide;

a shaft extending from the housing coaxially through the access guide; and a distal tip attached to the shaft and protruding from a portion of the access guide distal to the end effector.

13. The robotic surgical system of claim 12, wherein the tip is a rigid blunt tip, a retractable blunt tip, a rigid generally blunt tip with a central indexing point, a rigid sharp tip, or a retractable sharp tip.

14. The robotic surgical system of claim 12, wherein the access guide has a plurality of teeth disposed at the end distal to the end effector.

15. The robotic surgical system of claim 12, wherein the access guide has a smooth chamfer disposed at the end distal to the end effector.

16. The robotic surgical system of claim 12, further comprising a second guide interposed between the shaft and the access guide, wherein the locking buttons engaging the indents of the access guide traps the second guide between the housing and the access guide.

17. The robotic surgical system of claim 12, further comprising a second guide interposed between the shaft and the access guide, wherein the locking buttons prevent rotation between the housing and the second guide.

18. The robotic surgical system of claim 17, wherein the second guide has a plurality of indents in a portion of the second guide proximal to the end effector for engaging the locking buttons.

19. The robotic surgical system of claim 12, further comprising a second guide interposed between the shaft and the access guide, wherein the second guide has a pin for engaging a slot of the access guide, thereby preventing rotation between the housing, the second guide, and the access guide.

20. The robotic surgical system of claim 12, further comprising a second array attached to the initial access tool.

* * * * *